United States Patent
Suckau et al.

(10) Patent No.: US 7,070,949 B2
(45) Date of Patent: Jul. 4, 2006

(54) PROTEIN MIXTURE ANALYSIS BY MASS SPECTROMETRY

(75) Inventors: Detlev Suckau, Grasberg (DE); Peter Hufnagel, Bremen (DE); Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 280 days.

(21) Appl. No.: 10/303,651

(22) Filed: Nov. 25, 2002

(65) Prior Publication Data
US 2003/0124606 A1  Jul. 3, 2003

(30) Foreign Application Priority Data
Nov. 30, 2001 (DE) ............................... 101 58 860

(51) Int. Cl.
*C12Q 1/37* (2006.01)
(52) U.S. Cl. .................... 435/23; 435/7.1; 204/461; 514/2
(58) Field of Classification Search ................ 702/19
See application file for complete search history.

(56) References Cited

U.S. PATENT DOCUMENTS

| 5,885,841 | A | 3/1999 | Higgs, Jr. et al. |
| 5,903,003 | A | 5/1999 | Schubert et al. |
| 5,952,643 | A | 9/1999 | Cravatts |
| 6,300,627 | B1 | 10/2001 | Köster et al. |
| 2003/0089605 | A1* | 5/2003 | Timperman ............ 204/450 |

FOREIGN PATENT DOCUMENTS

| DE | 198 56 014 A1 | 12/1998 |
| DE | 199 37 438 A1 | 8/1999 |
| EP | 1 151 793 A1 | 11/2001 |
| GB | 2 342 498 A | 4/2000 |
| WO | WO 00/11208 A1 | 3/2000 |

OTHER PUBLICATIONS

Opiteck et al. Comprehensive Two-Dimensional High-Performance Liquid Chromatography for the Isolation of Overexpressed Porteins and Proteome Mapping. Analytical Biochemistry 1998. vol. 258, pp. 349-361.*

Zeng et al. Determination of N-Linked Glycosulation of Yeast External Invertase by Matrix-assisted Laser Desorption/Ionization Time-of-Flight Mass Spectrometry. Journal of Mass Spectrometry 1999. vol. 34, pp. 311-329.*

Yates, J. Mass Spectrometry and the Age of the Proteome. Journal of Mass Spectrometry 1998, vol. 33, pp. 1-19.*

Hoffman et al. Continuous free-flow electrophoresis separation of cytosolic proteins from the human colon carcinoma cell line LIM 1215: A non two-dimensional gel electrophoresis-based proteome analysis strategy. Proteomics, 2001. vol. 1, pp. 807-818.☐☐*

Gygi et al. Quantitative analysis of complex protein mixtures using isotope-coded affinity tags. Nature Biotechnology. vol. 17, Oct. 1999, pp. 994-999.*

Spengler. Post-source Decay Analysis in Matrix-assisted Laser Desorption/Ionization Mass Spectrometry of Biomolecules. Journal Mass Spectrom. 1997 vol. 32, pp. 1019-1036.*

Mann, M., "Useful Tables of Possible and Probable Peptide Masses", 43rd ASMS Conference on Mass Spectrometry and Allied Topics, European Molecular Biology Laboratory, p. 639.

Gay, Steven et al., "Modeling peptide mass fingerprinting data using the atomic composition of peptides", Electrophoresis, 20, WILEY-VCH Verlag GmbH, 1999, pp. 3527-3534.

Gobom, Johan et al., "α-Cyano-4-hydroxycinnamic Acid Affinity Sample Preparation. A Protocol for MALDI-MS Peptide Analysis in Proteomics", Analytical Chemistry, American Chemical Society, pp. A-E.

* cited by examiner

*Primary Examiner*—Christopher R Tate
*Assistant Examiner*—Marcela M Cordero Garcia

(57) ABSTRACT

The invention relates to the analysis of complex protein mixtures such as entire proteomes, and in particular the rapid detection of previously unknown or unusually expressed proteins by common enzymatic digestion, subsequent chromatographic separation and analysis of the digestion peptides by mass spectrometry. The invention consists in subjecting fractions of the digestion peptides separated by liquid chromatography to analysis by mass spectrometry, at a time other than that of the chromatography, in a tandem time-of-flight mass spectrometer with ionization by matrix assisted laser desorption (MALDI). This method finds many times more proteins than are found through the procedures predominantly used until now of two-dimensional gel electrophoresis with subsequent time-of-flight mass spectrometry. It also removes the time pressure that dominates the real-time analysis of coupled LC-MS processes, and it allows measurements to be reduced to the interesting proteins by intermediate analysis.

20 Claims, No Drawings

PROTEIN MIXTURE ANALYSIS BY MASS SPECTROMETRY

FIELD OF THE INVENTION

The invention relates to the analysis of complex protein mixtures, such as entire proteomes, in particular the rapid identification of previously unknown or unusually expressed proteins through common enzymatic digestion, subsequent chromatographic separation and analysis by mass spectrometry of the digestion peptides.

BACKGROUND OF THE INVENTION

A proteome is defined as the totality of all the proteins of one cell type under precisely defined boundary conditions. Because higher life forms contain several hundred types of cells, there are also hundreds of proteomes. At the same time, there are proteins that are common to all the cell types of the life-form (housekeeping proteins), and those that are specific to one type of cell. The proteome, moreover, is not unchangeable, being modified both qualitatively and quantitatively with boundary conditions such as age, or stress on the cell community resulting from the administration of medication.

Of special interest, of course, are the proteins of a proteome that are not yet known, both for their application as pharmaceutical target proteins and also as possible independent active substances, i.e., proteins suitable for pharmaceutical use. (Insulin provides one example of a protein suitable for pharmaceutical use; there are, however, many other examples.) Those proteins that may be suitable as active substances are in most cases only present in very small concentrations, and frequently escape the classic methods of proteome analysis.

Also of great value for understanding the function of cell communities are those proteins whose quantity changes when the cell community is stressed, such as through age, the administration of medicine, or diseases.

It is estimated that mammals possess well over 100,000 proteins, whose structural plans are to be found in somewhere between 30,000 to 40,000 genes. There are estimates which indicate that from one gene alone, the process of "splicing" gives rise, as a statistical average, to about three and a half different types of protein; on top of this, many more proteins are created through post-translational modifications. A proteome contains from some thousands up to some tens of thousands of proteins. Not even half the human proteins are known today.

Current analytic procedures for the proteins of a proteome are generally based on separating the dissolved proteins by 2D gel electrophoresis, punching out the dyed proteins, enzymatic digestion in gel chips, followed by MALDI mass spectrometry of the digested peptides in time-of-flight mass spectrometers, permitting both the precise masses of the digestion peptides to be obtained, as well as the daughter ion spectra of the digestion peptides in a rather complex process using what is known as the PSD (post source decay) method. The precise masses of the digestion peptides allow the proteins to be found in protein sequence databases, assuming that they are included in the database. If the identification is ambiguous, daughter ion spectra from individual digestion peptides can be exploited. If the protein is not contained in the protein sequence database, it is also possible to search in EST data (expressed sequence tags) that has been obtained from RNA, in cDNA data or in the DNA data of the genome.

This procedure has the advantage that the association of the digestion peptide with a protein is guaranteed by the procedure itself, at least in cases where the separation by 2D gel electrophoresis was of sufficiently good quality. However, from one protein, generally somewhere between 10 and 70 percent of the sequence is covered by the digestion peptides; in most cases rather under 50 percent. This is referred to as coverage. If the protein is contained in the database, then, as has already been described, knowledge of the precise masses of some digestion peptides is often sufficient for identification; in the case of ambiguous results, which most often occur when the mass determination is insufficiently precise, then an additional daughter ion spectrum of the peptide, characterizing its sequence of amino acids, yields certain identification.

It is perfectly possible for several thousand spots to be dyed and found in the 2D gel, although it is then found in the course of analysis that only at most about a thousand (and in most cases only a few hundred) different proteins can be analytically found in a proteome using this procedure. A proteome, however, is expected to include many times this number of proteins.

Another analytic procedure that has been introduced involves the analysis of mixtures of a few proteins by the digestion of all the proteins of this mixture, liquid chromatographic separation of the digestion peptides, ionization by electrospraying (ESI) and automatic MS/MS procedures for peptide structure determination in ion trap mass spectrometers or quadrupole-quadrupole time-of-flight mass spectrometers.

This common digestion of the proteins and the liquid chromatographic separation mean that the association of peptides with one protein is no longer given by the analytic procedure, and the association of various digestion peptides with a protein can only be made by the database search. Very good programs have now been developed for searching the databases and for searching for the peptides associated with a protein.

This procedure of real-time LC/MS analysis runs in ion trap mass spectrometers or in time-of-flight spectrometers with orthogonal injection and with preliminary separation and fragmentation in upstream quadrupole filters. These devices have a recording time for daughter ion spectra of somewhere between one and two seconds. It is therefore only possible to record at most five, but most often significantly fewer, different daughter ion spectra in a high resolution liquid chromatogram with a peak width of about 10 seconds. These procedures are therefore restricted to protein mixtures of low complexity. Mixtures with around five or ten proteins can be effectively analyzed, but more complex mixtures, such as an entire proteome with several tens of thousands of proteins, or even just part of a proteome with a few thousand proteins cannot be analyzed in this way. The applicability of frequently employed the procedure of real-time LC/MS analysis is restricted by the time pressure resulting from the chromatography. Even what are known as "stop-flow" methods are only of limited help, as they impair the separation capacity of the chromatography.

SUMMARY OF THE INVENTION

The invention is directed to subjecting fractions of the digestion peptides separated by liquid chromatography to analysis by mass spectrometry at a time other than that at which the chromatography takes place in a tandem time-of-flight mass spectrometer with ionization by matrix supported laser desorption (MALDI). This procedure discovers many times the number of proteins that are found by the procedure predominantly used until now of two-dimensional gel electrophoresis with subsequent time-of-flight mass spectrometry. Furthermore, it overcomes the time pressure to which real-time analysis in coupled LC-MS processes is subject, and it permits intermediate evaluations that can then reduce measurements to the interesting proteins.

It is possible with the invention to find and to identify considerably more proteins in a mixture of proteins than is possible with the procedures in use so far. It is also possible to identify those proteins that are of interest for the particular analytic task while the analysis is still proceeding, and to distinguish them from the large number of uninteresting proteins in the mixture. One can then exploit this knowledge of the interesting peptides in order to restrict the number of spectra that are to be measured to achieve the purposes of the particular analysis.

The procedure for analysis by mass spectrometry of a complex mixture of proteins having different amino acid sequences in accordance with the invention consists of the following steps:

a) joint enzymatic digestion of all proteins in the protein mixture is carried out, b) the peptides in the mixture are separated by liquid chromatography, preferably into the highest resolution columns possible, c) fractions from the chromatographic separation are collected separately, preferably a very large number of individual fractions (1000 to 3000); for very complex mixtures, a relatively large number of digestion peptides (20 or 30) still have to be found in each fraction, d) the mixtures of digestion peptides from the individual fractions are each prepared at one location of a sample sample support for a time-of-flight mass spectrometer, together with matrix substance, e) the digestion peptides from the samples are ionized by matrix assisted laser desorption (MALDI), the flight times of the ions are measured in the time-of-flight mass spectrometer, and from these flight times the masses of the digestion peptide ions are determined (the spectra generated here are called digestion peptide spectra), f) the daughter ion spectra of all or of selected digestion peptide ions from the samples are measured using MALDI tandem time-of-flight mass spectrometry, daughter ions being ionized fragments of the digestion peptide ions, and g) the associated proteins are identified by searching in protein sequence, EST, cDNA or DNA databases.

The fundamental distinction between this procedure and the procedure described above in which liquid chromatography is coupled with tandem mass spectrometry lies in the fact that neither the digestion peptide spectra nor the daughter ion spectra are measured as the chromatography proceeds, but at a later time point, decoupled both in time and in terms of the measuring instrument. In this way, if the mass spectrometer measures with sufficient sensitivity and if the supply of substance in the sample is sufficient, all the digestion peptides are subjected in succession to measurement of daughter ions, without the time pressure inevitably resulting from the chromatography playing a role. Also, all the digestion peptide spectra are measured first in this case; these can be evaluated, and only then are the daughter ion spectra measured, and these can also be processed in any desired order. This highly significant difference from real-time LC-MS analysis permits the measurement of daughter ion spectra to be restricted to those created from the interesting peptides.

In contrast to separation through 2D gel electrophoresis, something like four to five times as many proteins are found in one proteome if the procedure in accordance with the invention is used. Following a successful search in protein sequence, cDNA or genome databases, suitable programs assemble the digestion peptides together again into proteins.

It is not necessary that an entire proteome be digested together as a protein mixture in step (a); it is often advantageous to perform an initial coarse separation into partial proteomes. It is advantageous here to use sub-cellular partial proteomes, such as can, for instance, be prepared by breaking up a cell community mechanically or with the aid of ultrasound followed by centrifuging. These sub-cellular partial proteomes then each contain the proteins of individual cell elements, for instance the proteins of specific organelles such as the cell nucleus, lysosomes or the Golgi apparatus. It is also, however, possible to create partial proteomes through chromatography or electrophoresis, in particular through "free flow electrophoresis". Partial proteomes prepared by affinity extraction of protein groups are also of particular interest.

It is, in particular, possible for the protein mixture jointly digested in step (a) also to consist of a mixture of the same partial proteomes of two cell communities subject to different stresses, whose proteins were, before the mixture, at least partially modified by markers that can be distinguished by mass spectrometry. A combination of modifications of the proteins from two cell communities with affinity extraction can, in particular, be carried out by obtaining a derivate from the proteins with "isotope coded affinity tags" (ICAT). The affinity extraction can be applied to the proteins before the digestion, but is preferably applied to the digestion peptides following the digestion, that is between steps (a) and (b). This method can in particular be applied to the study of quantitative protein expression differences in two different proteomes, such as one from a healthy and one from a stressed cell community (R. Aebersold et al., WO0011208). The stress may, for instance, be caused by aging, temperature, chemical treatment (medication) or disease.

Collecting the chromatographic fractions in step (c) can advantageously occur directly on the sample support plate, to which matrix substances with an affinity for peptides and having the lowest possible solubility in water have already been applied. The preparation in step (d) may then, for instance, consist of subsequent washing processes and insertion of the digestion peptides into the small matrix crystals by briefly initiating solution of the small crystals with a suitableorganic solvent. Collection of the fractions on the sample support plate in particular means that the sequence coverage of the proteins by the peptides found is better than that achieved by the procedure of separating with 2D gel electrophoresis and subsequent MALDI time-of-flight mass spectrometry.

In step (f) it is possible to subject each of the peptides from a sample to measurement of their daughter ion spectra. For samples containing a large number of peptides, however, it is possible that the sample would become exhausted. It can therefore be advantageous to apply an intelligent selection procedure so that only those peptides helpful for the analytic procedure will have the spectra of their daughter ions measured.

If the purpose of the analytic procedure is to discover new, unknown proteins not contained in a reference protein sequence database, then the following intelligent selection procedure is suggested in the context of the objective of the invention:

Following step (e) the masses of all the digestion peptides from all the samples on the sample support plate are known. A program is now used first to select those samples that only contain a small number of digestion peptides, for instance a maximum of four digestion peptides. These are now subjected, in a first measurement pass, to measurement of the daughter ions. Each time a daughter ion spectrum is measured, this is passed to a search engine that looks for the associated protein in the protein reference database. Because a search based on this kind of spectrum is extraordinarily specific, identification is in nearly all cases unambiguous, provided the protein is present in the database. The protein structure found by a search engine is then subjected in a computer program to virtual digestion according to the known rules for the enzyme used, the masses of the digestion peptides are calculated, and peptides with these masses are marked as already known in the list of all the measured masses from all the samples. It is additionally possible to calculate from the known structure of the virtual digestion peptides their chromatographic retention times, which allows targeted restriction of the markings within the very large number of peptide masses.

After the samples with small numbers of peptides have been processed in a first measuring run, those samples in which only a small number of peptides marked as unknown remain can now be selected for the second measuring run. In this way, the number of peptides requiring measurement of the daughter ion spectra is reduced further and further in subsequent measuring runs. Finally, even for samples containing a very large number of peptides, only a moderately large number of peptides remain for measuring the daughter ion spectra.

All those peptides that do not belong to known proteins in the database belong to unknown proteins, which must then be subjected to a search in an EST, cDNA or genome database in order to identify them and determine where they belong. If this search is also unsuccessful, the data can be subjected to an entirely fresh sequencing process.

If the digestion peptides from a chromatographic run are not located on a single sample support plate it is also possible again here to change the sample support plates so that the mass spectra of the digestion peptides are measured first and then the daughter ion spectra of the digestion peptides. It is particularly advantageous if the different sample support plates are also analyzed simultaneously on different mass spectrometers, in which case the exclusion markings for the known peptides can be carried out jointly for all the samples on all the sample sample supports.

For the expression analysis of mixtures of two proteomes or partial proteomes, the intelligent selection of the daughter ion spectra to be measured can be based on the intensity differences between the peptides which are the same in each case apart from their different isotopic markers. Here again it is possible for the number of daughter ion spectra that it is necessary to measure to be reduced through knowledge of the identity of the proteins based on the daughter ion spectra of individual digestion peptides.

It should be emphasized at this point that the intelligent selection of the digestion peptides for the measurement of their daughter ion spectra, whether for the purpose of searching for unknown proteins, or for the study of expression differences in differently stressed cell communities, is only made possible through the separation of the chromatography and the subsequent tandem time-of-flight mass spectrometry in accordance with the invention.

DETAILED DESCRIPTION

An embodiment of the procedure is first described here in detail, which begins with sub-cellular partial proteomes and is particularly aimed at the rapid discovery of previously unknown proteins that are not contained in a reference database of protein sequences. The analytic objective is thus to discover unknown proteins.

In this embodiment the cell components of a community of cells are released, for instance through ultrasonic disintegration with the addition of detergents, and separated in a centrifuge into a number of partial proteomes, causing the various organelles to be separated due to their varying densities. It is not difficult to prepare 10 or 20 partial proteomes. The separation is selected, wherever possible, in such a way that an approximately equal number of proteins is found in each partial proteome; this is not, however, essential. Experience shows that the proteins in the partial proteomes are most often characteristically different so that, apart from a group of ubiquitous proteins, specific proteins are found in the various partial proteomes. The proteins are then made soluble in the usual way, such as by treatment with urea, and dissolved in water.

A sub-cellular partial proteome can, however, also be prepared from starting material other than cell communities, such as from a single cell. Equivalent partial proteomes can also be manufactured from blood or cerebrospinal fluid.

The partial proteomes are then subjected to tryptic digestion, each of them giving rise to some thousands or tens of thousands of digestion peptides. "Tryptic" digestion is digestion by the enzyme trypsin, which specifically cuts each of the C-terminals of the two basic amino acids lysine and arginine. The digestion peptides have mean sizes of about 10 amino acids (depending slightly on the statistical proportions of lysine and arginine in the proteome). The lengths have a Poisson distribution extending from one amino acid up to about 40 amino acids. The majority of peptides have a mass in the range of between 800 and 4000 atomic mass units, and these can effectively be measured by MALDI time-of-flight mass spectrometry. The digestion peptides cover the range between extreme hydrophilia and extreme hydrophobia relatively evenly.

The digestion peptides of these partial proteomes are each subjected to a slow, high-resolution liquid chromatography process, in which a flow rate of, for example, around 10 to 20 microliters per minute is set. A form of reversed phase chromatography is selected, which primarily separates according to hydrophobia or hydrophilia. This yields a relatively even separation of the digestion peptides over time. Chromatography at 10 to 20 microliters per minute is considered to be a relatively easily managed form of chromatography. Depending on the quantity of original material from which the proteome or partial proteome is extracted, other types of liquid chromatography may also be used, such as a micro or nano liquid chromatography.

The eluate from the chromatographic column is passed directly through a narrow capillary tube to a mass spectrometry sample support plate. In the case of micro or nano liquid chromatography it is beneficial to apply the eluate to the sample support plate by means of a droplet dispenser such as a piezo electric dispenser, since the flow rates are lower in this case.

There are commercial time-of-flight mass spectrometers that process sample support plates having the size of microtitration plates. Such sample support plates can be prepared with thin layers of small matrix crystals on 1536 hydrophilic anchors (whose diameters may be between 200 and 1000 micrometers) each surrounded by hydrophobic areas before the eluate is applied. During the chromatography, between 1 and 2 microliters of eluate is applied to these anchors over a period of, for example, around six seconds. In this process a robot generates the relative movement between the sample support plate and the capillary ends. The layer of matrix crystals bonds the digestion peptides strongly enough that they can subsequently be carefully washed in water. So that the droplets on neighboring anchors, which are only 2.25 millimeters apart, are not at risk of running into one another through insufficient separation, it is possible to apply eluate only to every second row of anchors on the plate. The gaps are filled in later, when the droplets first applied have dried.

-cyano-4-hydroxycinnamic acid can, for example, be used as the matrix substance. This substance is not soluble in water, and after having been applied from a solution of acetonitrile or acetone forms a thin layer of a very small crystals on the surface of the sample support plate, and bonds the digestion peptides firmly to its surface (see J. Gobom et al., "-Cyano-4-Hydroxycinnamic Acid 80 Affinity Sample Preparation. A Protocol for MALDI-MS Peptide Analysis in Proteomics.", Anal. Chem. 2001, 73, 434–438). On suitable support plates it is possible, for instance, for 1536 small sample spots, to each of which such a thin layer of matrix has been applied, to be loaded with samples from one fraction each. The eluate with the digestion peptides is applied with the aid of a robot directly from the movable separation capillary tube of the liquid chromatograph to the thin crystal layers. It is favorable if the droplets are removed about 30 seconds after having been applied using a suction pipette or with filter paper to prevent impurities from drying on.

If the chromatography takes about 2.5 hours then, at a cycle rate of six seconds, it is just possible to fill one sample support plate with 1536 anchors. If there are, for example, 12 partial proteomes, then it is possible using four chromatographs for the chromatography to be completed in one working shift, and to create 12 sample support plates each bearing one partial proteome. The various digestion peptides from a protein are in this case each located on only one sample support plate, even if in quite different fractions. This is important for the subsequent marking of already known peptides.

Once the chromatography is complete, the dried plates can be washed in deionized water (acidified with trifluoroethanoic acid to give a 0.1 molar solution concentration) in order to remove all the remaining salts and buffer substances left over from the chromatography. The digestion peptides, however, remain bonded to the matrix crystals. After the washing and drying, about half a microliter of solvent (ethanol:acetone:formic acid 6:3:1, for instance) is pipetted onto each sample in order to substantially dissolve the matrix crystals again. The matrix substance re-crystallizes very quickly due to the rapid evaporation of the solvent, and thus incorporates the digestion peptide molecules into its crystal structure. They are then ideally suited to subsequent analysis by mass spectrometry with ionization by matrix assisted laser desorption (MALDI). This kind of treatment avoids the use of intermediate containers in which digestion peptides are inevitably lost through becoming attached to the container walls.

The sample sample supports are transferred to the mass spectrometer's vacuum system. Here a pulsed, focussed laser beam is fired at each of the samples, causing the digestion molecules to be ionized by what is referred to as proton transfer in a small cloud of plasma consisting mainly of matrix molecules and a few matrix ions. The peptide ions are then accelerated into the mass spectrometer's flight tube. Their time of flight up to an ion detector is measured very precisely in the mass spectrometer. In a reflector time-of-flight mass spectrometer, approximately 1.5 meters long, the flight time can be measured to within an accuracy of a few hundred picoseconds, which yields a precision of about 10 to 20 parts per million (ppm) for the mass determination. In each sample, in other words in each chromatographic fraction, there are, if the procedure has been ideally executed, somewhere between three and thirty such digestion peptides.

While the spectra of digestion peptides is being recorded, the spectra from the respective previous recordings are already being converted from flight times to masses. Each digestion peptide has an isotope pattern, and these are also taken into account here. As described in DE 198 03 309, this increases the precision of the mass determination, and this is found for just one mass of the isotopic group, the mass of the so-called monoisotopic peak. It is also this mass that is used by the search engines. In order to increase the mass precision, it is also possible, if necessary, in some cases to employ the masses of reference substances, which can be applied to the matrix substance anchors before the chromatographic application of the digestion peptides. In another procedure for improving the accuracy of mass determination, reference samples in the neighborhood of the samples that are to be evaluated are used. It is thus possible to occupy 24, 48 or 96 anchors, distributed evenly amongst the 1536 anchor areas, with reference samples that can be used for the mass determination in order, for instance, to be able to compensate for slight unevenness in the sample support plate that affect the flight times. These anchors containing reference substances are omitted when the digestion peptides are applied.

Furthermore, during the acquisition of the digestion peptide spectra, sample anchors to which successive samples have been applied are examined to see whether a digestion peptide occupies a number of MALDI samples, because the digestion peptide forms a temporally wide chromatographic peak that spreads over two or more samples. In such cases the sample with the most intense spectrum is selected for the later recording of daughter ion spectra. The masses of the digestion peptides in the other samples are marked in a list of all the digestion peptides in all the samples as not being worthy of evaluation.

Over the last two years, new principles (see for instance patent specification DE 198 56 014 A1 and the equivalent U.S. Pat. No. 6,300,627) and new mass spectrometers of the MALDI tandem time-of-flight mass spectrometer type have been developed for recording daughter ion spectra, which are both fast and particularly sparing in the quantities of substance consumed. The generic abbreviation TOF/TOF has now become accepted for these devices. These tandem time-of-flight mass spectrometers consist of a first time-of-flight mass spectrometer that selects decomposing parent ions and the daughter ions that are thus created, and which excludes all the other ions, and a second time-of-flight mass spectrometer which, with the aid of subsequent acceleration of the daughter ions that have been created, analyzes their mass from their times of flight. MALDI tandem time-of-flight mass spectrometers with orthogonal ion injection are also very new. Here the first, ion selecting mass spectrometer is a quadrupole filter that is followed by a quadrupole collision chamber for the fragmentation of the ions. The abbreviation MALDIQ-TOF has become accepted for these devices.

Without these two types of new MALDI tandem time-of-flight mass spectrometer, the present invention could not be implemented.

Daughter ions are ionized fragments of the digestion peptide ions, and they can be obtained by laser-induced metastable decomposition of the digestion peptide ions, or collision-induced in a collision chamber. Because the fragmentation usually follows very simple rules, at least a partial sequence of the amino acids in the peptide can be obtained from the daughter ion spectrum of a digestion peptide. The search engines can, however, use the daughter ion spectra for protein identification even without determining a partial sequence.

In spite of the fact that these new devices use a recording process that consumes much less substance than former procedures, it is possible for the available substance in a sample to be exhausted before all the daughter ion spectra have been recorded in samples that contain an unusually large number of digestion peptides. It is therefore also the purpose of the invention to develop a strategy that reduces the number of daughter ion spectra to be recorded for a sample and to select the correct peptides for the measurement of daughter ion spectra.

Once the digestion peptide spectra (not yet the daughter ion spectra) of all the samples are measured, then the lists of measured peptides, which now contain the monoisotopic masses and markings of appropriateness for evaluation, are subjected to a further investigation while the time-of-flight mass spectrometer at the same time is automatically readjusted for operation that will record daughter ion spectra. This investigation establishes how many digestion peptides worthy of investigation are found in the individual samples. At this stage those samples that only contain a small number of peptides worthy of evaluation, a maximum of four, for instance, are marked for immediate evaluation in a first measurement run for daughter ion spectra.

After the mass spectrometer has been readjusted to record daughter ion spectra, a process that requires a few minutes in order to stabilize the newly adjusted electronic voltage supplies, the daughter ion spectra of the digestion peptides are measured for all those samples that have been marked for immediate evaluation. As soon as each daughter ion spectrum has been recorded, it is immediately passed to a search engine for a protein search in the reference protein sequence database. The search engine is a program for intelligent searching in the database for a protein that contains this digestion peptide. This search is usually entirely unambiguous, because the daughter ion spectra of the digestion peptides are very specific to their proteins. It is also immediately clear whether the associated protein exists in the database or not. The search, which is normally performed on a server dedicated specifically for this purpose, is executed very quickly, and usually takes only about one second.

The "SwissProt™" database from GeneBio (Geneva Bioinformatics S.A.), Geneva, which is always kept up to date, can, for instance, be used as the protein sequence library for the known proteins. There are, however, also other databases that can be used here, such as the NCBInr database from the National Institute of Health, USA, that contains genome data in addition to the protein data. The "Mascot™" program from Matrix Science Ltd., London, may be mentioned as a search engine, but here again there are a number of comparable search engines on the market. The search can be carried out over the internet, or within the organization (by intranet) if the database and the weekly database updates have been downloaded onto a local server (following the conclusion of appropriate contracts).

If an associated protein is found, then this protein is known, and thus, in accordance with the purposes of the analysis assumed here, uninteresting for further analysis. The structure of this protein is then extracted from the database, "virtually" digested by a program, and the precise masses of the virtual digestion peptides are calculated. The hydrophobicity of these virtual peptides is also found on the basis of their composition and their sequence of amino acids. From the hydrophobicity, a reasonably good determination of the retention time of this peptide for the "reversed phase" chromatography can be made. All the masses of the real digestion peptides in the relevant retention time window are now compared to detect the occurrence of a peptide having the mass of the virtual digestion peptide. If such a peptide is found, then it is marked as known, and excluded from further investigations. Incorrect markings here are quite rare, but can be further reduced through a confirmation process.

Even the number of a protein's peptides found in a daughter ion spectrum provides a confirmation that the identification is correct. It is, however, also possible to permit a second digestion peptide from the same protein to be used for measurement of the daughter ion spectrum for the sake of confirmation, preferably one that is also located in a sample with only a few peptides. If the identification is doubtful, the markings can be removed.

When all the MALDI samples selected for the immediate first investigation by recording the daughter ion spectra have been measured (as a reminder, these are the samples that contained at most four peptides suitable for evaluation), then in this way the number of daughter ion spectra still to be measured in the remaining MALDI samples has already been considerably reduced. A computer program now investigates which of the remaining samples now only possess a small number of digestion peptides for the recording of daughter ion spectra in a second measurement run i.e. have peptide masses that have not been marked as uninteresting for measurement or as belonging to a known protein. In successive measurement runs, the number of daughter ion spectra to be measured is thus reduced further and further, so that even for those samples that possess a large number of peptides, the number of peptides requiring evaluation is reduced to an acceptable level.

All those peptides that do not belong to proteins known in the database belong to the unknown proteins that are being sought. For their identification, and in order to determine the proteins to which they may be long, they are finally subjected to a search in a cDNA or DNA database. The EST databases (expressed sequence tags) are available as cDNA databases, although they do not usually contain the complete sequence of the protein. Complete cDNA databases are, however, being constructed. As DNA databases, the genome databases, most of which are available on the internet, are reasonably complete for a number of species (including human beings).

This exclusion procedure not only counters the risk of exhausting a fraction, i.e. a MALDI sample, but the entire measurement time is considerably reduced.

With an average of ten daughter ion spectra for each sample, and a duration of approximately ten seconds required to record the spectrum of each digestion peptide, the entire measurement of one sample would take on average almost two minutes, and the measurement of all 1536 fractions containing about 15,000 digestion peptides in fully automatic operation would require about two full days. This applies at present to commercially available devices. It is to be expected for future further developments that the 1536 fractions on one sample support plate can be recorded in about 12 hours under the above conditions. This time is extremely long. However, if the number of daughter ion spectra is reduced by the intelligent selection process to about four spectra on each sample, then the analysis of a proteome or partial proteome on a sample support plate using future devices will be possible in less than about six hours.

The 12 sample support plates with the partial proteomes in our example could then be measured in three days, if the sample support plates are fed through automatically. This time is still very long, because the sample quality on the sample support plates slowly deteriorates as the days go by. It is therefore advisable for this purpose to use three mass spectrometers in parallel, to complete the analytic task within one day. Searching through a proteome for a new protein has never been achieved in such a short time.

The number of proteins that can be found following this procedure is several times greater than could be found with the procedures used up to now. The coverage of the proteins with digestion peptides is also greater. This means not only that more proteins than before can be found within a proteome, but also that more differences to the sequences present in the databases can be found. This makes the procedure many times more powerful than the procedures used up to now.

There are many possible variations to this procedure.

It is, for instance, possible for the chromatographic fractions to be temporarily collected in fraction collectors before they are applied, together with matrix substances, to the sample support plates. Some chromatographs can be fitted with this kind of fraction collector; the fraction collection containers can also, however, irretrievably adsorb hydrophobic digestion peptides on the walls.

It is, not necessary for the fractions to be collected over equidistant time periods. With modern operating systems for chromatographs it is possible to divide the fractions in accordance with the frequency of the peaks or according to a total ion current. The occurrence of peaks or the total ion current can be determined here either by means of UV detectors or by mass spectrometry of part of the eluate current.

The procedure can also be subjected to a further chromatographic stage in order to reduce the number of digestion peptides in each fraction, for an analytic task aimed, for instance, at tracing structural differences in the real proteins of the mixture from those in the database. This can make the mass spectrometry measurement procedure more sensitive, because each time the daughter ion spectrum from a digestion peptide is recorded, the other digestion peptides are also vaporized, thus destroying substance for further analysis. This kind of chromatography can for instance place the individual fractions cyclically in just 20 collective fractions. This creates collective fractions that contain, for instance, the first, the 21st, the 41st, the 61st fraction and so on. The 20 collective fractions can then be subjected to chromatography again using a different column material to achieve an even peak distribution.

Another extremely interesting procedure combines a second chromatography with a modification of all or some of the digestion peptides, for instance by oxidation of methionine, by enzymatic deglycosylation or similar procedures, between the first and second chromatographic processes. If a fraction from the first chromatographic run modified in this way is subjected to a second chromatographic run in a column of the same type, then the modified peptides are shifted in comparison with the unmodified peptides, and the modified peptides can be selectively further processed.

Application of the fractions to the sample support plates can be carried out differently than described above. The sample supports can have small hydrophilic anchor areas with diameters of about 300 micrometers, surrounded by rings with widely affinitive thin layers having a diameter of about 800 micrometers and surrounded in turn by strongly hydrophobic areas. High affinity thin layers with wide ranging adsorption may, for example, consist of superficially bonded C18 chains; i.e., alkyl chains with 18 carbon atoms covalently bonded to the metallic surface. If drops containing about one microliter of eluate are applied here, they cover the high affinity rings, and a wide range of peptides, i.e., from very hydrophilic through to very hydrophobic peptides are bonded. After washing and drying, the peptides can be desorbed again using acetonitrile with five percent water and some dissolved matrix substance. As it dries, the applied liquid retreats to the hydrophilic anchors, where the matrix crystals then form, incorporating some of the peptides into themselves.

A second preferred embodiment of the procedure in accordance with the invention, which will be described here in some detail, is relevant to an analytic task whose aim is to quantify the expression of proteins. Analysis of the differences in the expression of proteins in two differently stressed cell communities is of particular interest. This can be used to determine the reaction in the cells to external or internal stress conditions, and provide insight into the behavior and functioning of the cells. The stress can be created through aging of the cell community, through the effect of temperature, through the effect of chemicals, in particular medicines, or through a variety of sicknesses of the cell community or of the parent organism.

For this study it is again advisable to investigate sub-cellular partial proteomes. Sub-cellular partial proteomes are therefore prepared from normal and from stressed cell communities. The dissolved proteins in the two proteomes are now modified before being mixed, in such a way that the modifications can be distinguished by mass spectrometry, so that the association of a protein with one or the other partial proteome can still be recognized. The subsequent mixing then creates the protein mixture which is subjected to a joint enzymatic digestion in step (a) of claim 1 of the procedure in accordance with the invention.

A particularly favorable method has become known under the abbreviation "ICAT", which stands for "isotopically coded affinity tag".

An ICAT reagent for modification consists of (1) a reactive group that can react with a specific amino acid, for example the thiol group of cystine, (2) an affinity group, biotin for instance, that can be used for an affinitive extraction (in this case, for example, with streptavidine), and (3) a linker in two different isotopically marked forms.

In this way not only is a modification that can be distinguished through mass spectrometry carried out, but the modification is one that contains a highly specific affinity group, so that after the common digestion it is possible to extract the modified proteins and to separate them from the unmodified proteins or digestion peptides. Biotin, for instance, may be used as the affinity group; this biotin may, for instance, be bonded to a cystine with the aid of a linker and a reaction group. The linker contains 8 hydrogen atoms that are bonded so tightly that they cannot exchange themselves in solution. The isotope coding now consists in the linker having eight normal hydrogen atoms in one case, but eight deuterium atoms in the other case. The two modifications therefore differ by precisely eight atomic mass units.

It is advantageous for the marked digestion peptides now to be subjected to affinitive extraction between steps (a) and (b). The extraction can, for instance, be performed using small magnetic spheres whose surface is covered with streptavidine, and which bond the biotin groups affinitively. After washing, the marked digestion peptides can be released again from the streptavidine by carefully adding ammonia. The marked digestion peptides are now, as in the procedure described above, separated into individual fractions through liquid chromatography. The fractions are prepared on sample support plates. Mass spectra for the mixtures of digestion peptides in the individual fractions are recorded.

Because the isotope marking of the modifications does not result in differences in retention time, the same digestion peptides, differently coded, from the same proteins in the two partial proteomes are both found in the same fractions, and therefore in the same MALDI sample. If the two proteins are equally strongly expressed, then the digestion peptide spectra will contain two equally intense isotope groups, separated by precisely eight mass units (or, if there are two cystines in the digestion peptide group, precisely 16 units). In the light of the purpose of the analysis, equally intense groups are uninteresting, and it is rather those groups in which the intensities differ that are of interest. Sometimes only one group is found, and this can be a protein that is only generated in the stress situation, or that is no longer formed at all in the stress situation. The differences in the intensities can be used to select those peptides whose daughter ion spectra are to be measured. The daughter ion spectra in turn permit those proteins that exhibit different expressions to be identified.

Two preferred embodiments appropriate to analytic tasks with different purposes have been described here in detail, as well as a further embodiment, allowing the discovery of differences in proteins in the proteome from the proteins in the database. However, for the basic procedure, and also for the intelligent selection procedure, there are a wide range of variations that depend upon the purpose of the analysis. It is possible for an expert with knowledge of this invention to adapt it to his analytic purposes.

The invention claimed is:

1. Method for the analysis of a mixture of different proteins by mass spectrometry, comprising:
   a) digesting the different proteins in the protein mixture with a common enzymatic digestion;
   b) separating chromatographically the mixture of digestion peptides;
   c) collecting individual chromatographic fractions;
   d) preparing samples on a sample support, wherein the samples contain the digestion peptides from the fractions together with a matrix substance;
   e) ionizing the digestion peptides from the samples by matrix assisted laser desorption in a time-of-flight mass spectrometer, and measuring the times of flight to determine the masses of the digestion peptide ions;
   f) measuring the daughter ion spectra of at least some digestion peptide ions from selected samples by MALDI tandem time-of-flight mass spectrometry; and
   g) identifying the associated proteins by searching in at least one of a protein sequence, cDNA or DNA database.

2. Method according to claim 1 wherein the protein mixture is a proteome.

3. Method according to claim 1 wherein the protein mixture is a partial proteome.

4. Method according to claim 3 wherein the protein mixture is a sub-cellular partial proteome prepared by separation into sub-cellular fractions.

5. Method according to claim 4 wherein the sub-cellular fractions are separated centrifugally.

6. Method according to claim 3 wherein the partial proteome is prepared through coarse chromatographic or electrophoretic separation.

7. Method according to claim 6 wherein the coarse separation is carried out by means of "free flow electrophoresis".

8. Method according to claim 3 wherein the partial proteome is obtained by affinitive extraction from a proteome or partial proteome.

9. Method according to claim 1 wherein the protein mixture is a mixture of the proteins from two proteomes or partial proteomes, and wherein the association of at least part of the proteins with the two proteomes or partial proteomes can be detected through modifications that can be distinguished by mass spectrometry.

10. Method according to claim 9 wherein the modification also contains an affinitive group.

11. Method according to claim 10 wherein the modified proteins are subjected to affinitive extraction in order to separate them from the unmodified proteins or digestion peptides.

12. Method according to claim 9 wherein the modifications employ isotope coded affinity tags.

13. Method according to claim 1 wherein the individual chromatographic fractions in step c) are collected directly on a sample support plate to which matrix substance has been applied, and are prepared there in step d).

14. Method according to claim 1 wherein steps e) and f) are carried out in the same reflector time of flight mass spectrometer.

15. Method according to claim 1 wherein a list with exclusion markings is maintained for the digestion peptides of all the samples, excluding them from measurement of their daughter ion spectra.

16. Method according to claim 15 wherein peptides that are found at higher intensity in samples that were prepared beforehand or subsequently are marked for exclusion.

17. Method according to claim 15 wherein the peptides whose measured masses indicate that they belong to an already known protein that has been identified as being present in the protein mixture on the basis of the daughter ion spectrum of another digestion peptide are marked for exclusion.

18. Method according to claim 17 wherein a calculated retention time is considered in addition to the mass when determining markings for the exclusion of a peptide.

19. Method according to claim 15 wherein in determining the marking for exclusion from the measurement of daughter ion spectra, a comparison of the intensities of the same peptides that have been recognized through the modifications detectable by mass spectrometry as belonging to different proteomes or partial proteomes is considered.

20. Method according to claim 15 wherein the daughter ion spectra are each first measured in those samples that are only characterized by a small number of peptides that have not been marked for exclusion.

* * * * *